(12) United States Patent
Boehm et al.

(10) Patent No.: US 9,046,092 B2
(45) Date of Patent: Jun. 2, 2015

(54) INHALATION THERAPY DEVICE COMPRESSOR

(75) Inventors: Andreas Boehm, Reichling (DE); Martin Luber, Strasslach Dingharting (DE)

(73) Assignee: PARI GmbH Spezialisten für effektive Inhalation, Starnberg (DE)

(*) Notice: Subject to any disclaimer, the term of this patent is extended or adjusted under 35 U.S.C. 154(b) by 1282 days.

(21) Appl. No.: 11/724,588

(22) Filed: Mar. 15, 2007

(65) Prior Publication Data
US 2007/0215150 A1 Sep. 20, 2007

(30) Foreign Application Priority Data
Mar. 16, 2006 (DE) .......................... 10 2006 012 174

(51) Int. Cl.
F04B 39/12 (2006.01)
F04B 45/04 (2006.01)
A61M 11/06 (2006.01)
(Continued)

(52) U.S. Cl.
CPC .............. F04B 45/041 (2013.01); A61M 11/06 (2013.01); F04B 43/02 (2013.01); F04B 43/023 (2013.01); F04B 45/04 (2013.01); A61M 16/0063 (2014.02)

(58) Field of Classification Search
CPC ........ F04B 45/04; F04B 45/041; F04B 43/02; F04B 43/023; F04B 39/122; F04B 39/123; F04B 53/16; F04B 39/128; F04B 39/06; F04B 39/066
USPC .............. 417/418, 413.1, 395, 403, 404, 255, 417/560, 504, 515, 534; 128/203.12, 128/204.18, 205.13–205.15
See application file for complete search history.

(56) References Cited

U.S. PATENT DOCUMENTS 1,109,154 A * 9/1914 Thomas ......................... 417/255
1,445,073 A * 2/1923 Corpl et al. .................... 417/242
(Continued)

FOREIGN PATENT DOCUMENTS

CH       281 847 A      3/1952
DE    692 03 372 T2    12/1995
(Continued)

OTHER PUBLICATIONS

Search Report mailed May 7, 2007 from European Application No. 07005467.1-2315.
(Continued)

*Primary Examiner* — Peter J Bertheaud
(74) *Attorney, Agent, or Firm* — Wolf, Greenfield & Sacks, P.C.

(57) ABSTRACT

The compressor includes two compression spaces (1, 5) separate from one another, one of which serves to generate the continuous pressure medium flow for the generation of a basic aerosol flow, whereas the other is used to generate the pressure variations. The shared compression device (4), for example a piston, is moved in a pendulum motion by a drive (7) so that a gas is conveyed through the first compression space and pressure variations are imposed upon a gas volume via the second compression space. The drive is disposed in a compression space, use advantageously being made of the space volume available that may if necessary be made use of by the compressor. In a preferred embodiment the drive (7) is located in the compression space (5) that is used to generate the pressure variations.

15 Claims, 6 Drawing Sheets

Figure 1:
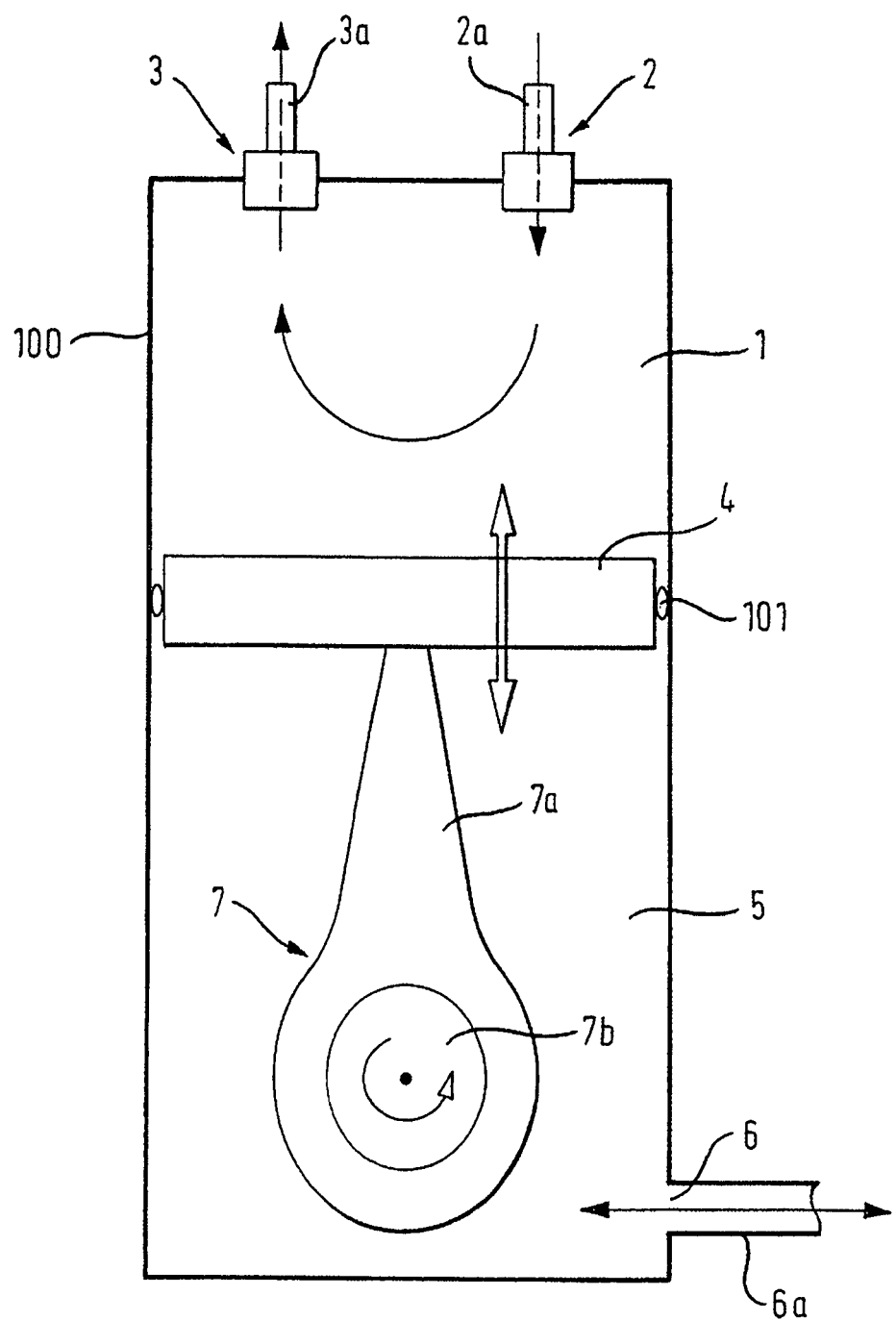

(51) Int. Cl.
 *F04B 43/02* (2006.01)
 *A61M 16/00* (2006.01)

(56) References Cited

U.S. PATENT DOCUMENTS

| | | | | |
|---|---|---|---|---|
| 1,874,752 | A | * | 8/1932 | Hirsch ................. 92/82 |
| 1,891,083 | A | * | 12/1932 | Dodge .................. 417/242 |
| 3,338,509 | A | * | 8/1967 | McAninch ............. 417/242 |
| 3,530,873 | A | * | 9/1970 | Arp et al. ............... 137/99 |
| 3,601,505 | A | * | 8/1971 | Bratsch .................. 417/46 |
| 3,947,156 | A | | 3/1976 | Becker |
| 4,468,177 | A | * | 8/1984 | Strimling ............... 417/413.1 |
| 4,836,198 | A | * | 6/1989 | Gates ..................... 128/205.18 |
| 4,898,165 | A | * | 2/1990 | Warzeka ................ 128/204.18 |
| 4,930,997 | A | * | 6/1990 | Bennett ................. 417/410.1 |
| 5,152,677 | A | * | 10/1992 | Bauer et al. ........... 417/366 |
| 5,683,232 | A | * | 11/1997 | Adahan ................. 417/440 |
| 6,131,406 | A | * | 10/2000 | Barowsky et al. ..... 62/505 |
| 6,514,177 | B1 | | 2/2003 | Brugger et al. |
| 6,547,749 | B2 | * | 4/2003 | Hansen .................. 601/48 |
| 8,308,447 | B2 | * | 11/2012 | Hartl ..................... 417/309 |
| 8,317,488 | B2 | * | 11/2012 | Hartl ..................... 417/309 |
| 2005/0224085 | A1 | * | 10/2005 | Zvuloni ................. 128/897 |
| 2006/0051219 | A1 | | 3/2006 | Becker et al. |
| 2006/0162722 | A1 | * | 7/2006 | Boehm et al. ......... 128/200.14 |

FOREIGN PATENT DOCUMENTS

| | | |
|---|---|---|
| DE | 195 19 763 A1 | 12/1996 |
| DE | 195 36 860 A1 | 4/1997 |
| DE | 22 11 096 A | 4/2001 |
| DE | 199 47 444 A | 4/2001 |
| FR | 2 639 236 A1 | 5/1990 |
| GB | 1 224 316 A | 3/1971 |
| JP | 2003-328952 A | 11/2003 |
| JP | 2005-188368 A | 7/2005 |
| JP | 2006-504020 A | 2/2006 |
| WO | WO 01/24858 A2 | 4/2001 |
| WO | WO 2004020029 A1 * | 3/2004 |

OTHER PUBLICATIONS

Official Action dated Nov. 15, 2006 from German Application No. 10 2006 012 174.0.

* cited by examiner

INHALATION THERAPY DEVICE COMPRESSOR

The invention relates to a compressor for inhalation therapy devices in which a therapeutically active fluid is nebulized by means of a gas supplied under pressure, generally by means of compressed air.

As described for example in EP 0 170 715 A, inhalation therapy devices of this type have, to nebulize the fluid, a pressure medium-operated nebulizing nozzle to which the pressure medium and the fluid is supplied. EP 0 170 715 A describes a nebulizing device in which the patient breathes in the generated aerosol via a mouthpiece. It is also known that, to treat the nasal cavity, the generated aerosol can be supplied directly to the nose of the patient, DE 102 39 321 B describing in detail how additional pressure variations can be superimposed upon the basic aerosol flow generated by the pressure medium and passing through the nose in order to achieve or assist penetration of the aerosol into the paranasal sinuses. Two compressors are needed for this, namely one compressor to generate the compressed air and one compressor to generate the pressure variations. Both compressors interact in such a way that, by means of an inhalation therapy device comprising a nebulizing nozzle, a basic aerosol flow is generated with superimposed pressure variations. The compressors used in inhalation therapy devices with nebulizing nozzle are generally electromotor-driven piston compressors or diaphragm compressors, such as described for example in DE 199 27 528 or in DE 102 39 321 B.

The cost involved in providing and handling two compressors is considerable and it has therefore already been proposed that only one electromotor should be used to drive both compressors and that both compressors together with the electromotor drive should be accommodated in one housing, thereby both reducing the manufacturing cost and simplifying the handling.

Seen against this background, it is the object of the invention to further reduce the cost in the above-described area and to provide a compressor that is, on the one hand, compactly structured and economical to manufacture and, on the other hand, that could be used both to generate a compressed gas flow to nebulize a therapeutically active fluid and also to generate pressure variations that can be superimposed upon an aerosol flow generated with the compressed gas flow. In addition, it must be possible for the compressor to be designed for therapeutic use.

This object is achieved with an inhalation therapy device compressor having

- a first compression space:
- a gas inlet means for the inflow of a first gas into the first compression space;
- a gas outlet means for the outflow of the first gas from the first compression space;
- a compression means that closes off the first compression space in such a way that, when the compression means moves, the first gas is conveyed into the first compression space via the gas inlet means and conveyed out of the first compression space via the gas outlet means;
- a second compression space;
- a gas passage opening for the escape of the second gas from the second compression space; and
- a movement means that is disposed inside one of the two compression spaces and that is associated with the compression means in such a way that the compression means can be moved by means of the movement means.

On the basis of the design according to the invention, the compressor comprises two compression spaces separated from one another, one of which serves to generate the continuous pressure medium flow to generate a main aerosol flow while the other is employed to generate the pressure variations. The shared compression means, for example a piston, is moved by a drive in pendulum fashion so that a gas is conveyed through the first compression space and pressure variations are superimposed upon a gas volume via the second compression space.

According to the invention the drive is disposed in a compression space, the invention advantageously using the space volume available that is necessarily taken up by the compressor. In a preferred embodiment according to the invention, the drive is accommodated in the compression space that is used to generate the pressure variations. This design is advantageous because the compression space that serves to generate the continuous pressure medium flow must be designed to be particularly tight because of the comparatively high pressures and flow rates. In contrast it is easier to locate the ducts that are needed for the drive through the compressor housing wall into the compression space in which the drive is positioned at the place where lower pressures occur, namely in the compression space in which the pressure variations are generated. Basically it is, however, also possible to position the drive in the compression space through which the pressure medium flow is conveyed if a corresponding tightness is guaranteed at apertures and ducts, for example the duct of the shaft of the electromotor.

Further advantageous embodiments can be seen from the sub-claims.

In the following, the invention will be explained in more detail by means of embodiments with reference to the figures, which show:

FIG. 1 a schematic view of a first embodiment;

FIG. 2 a schematic view of a second embodiment;

FIG. 3 a schematic view of a third embodiment;

FIG. 4 a schematic view of a fourth embodiment;

FIG. 5 a detailed view of a gas inlet means with inlet valve according to the invention;

FIG. 6 a detailed view of a gas outlet means with outlet valve according to the invention, and FIG. 7 a gas inlet means with gas inlet valve according to the invention.

FIG. 1 shows a first embodiment of the inhalation therapy device compressor according to the invention. In this embodiment, the compressor comprises a first compression space 1 that is surrounded by a housing 100 of the compressor. In the housing 100 there is provided a compression means 4 in the form of a piston that is equipped at its outer circumference to the housing 100 with a seal 101, for example of Teflon, and that closes off the first compression space 1 in the housing 100. With reference to the first compression space 1, the compressor shown in FIG. 1 also comprises according to the invention a gas inlet means 2, which permits a gas, for example, ambient air, to flow into the first compression space and prevents an outflow of the gas from the first compression space. For this purpose the gas inlet means 2 has an inlet valve that will be described in greater detail below. With reference to the first compression space 1 there is provided for the outflow of the gas from the first compression space 1 a gas outlet means 3 that enables the gas to flow out of the first compression space and prevents the first gas from flowing into the first compression space 1. For this purpose the gas inlet means 3 has an inlet valve that will be described in greater detail below. When the piston 4 is moved backwards and forwards in the housing 100 of the compressor according to the invention, as indicated by the double arrow in FIG. 1, the first gas, for example ambient air, is initially conveyed through the gas inlet means 2 into the first compression space 1 and then later conveyed out of the compression space 1 through the gas outlet means 3 due to the reverse movement of the piston 4.

In order to move the piston 4 in the housing 100 a drive is provided of which FIG. 1 shows a movement means 7 in the form of a connecting rod 7a and an eccentric plate 7b. The eccentric plate 7b is driven by an electromotor (not shown) so that the rotational movement of the eccentric plate 7b causes the connecting rod to move the piston 4 backwards and forwards in a pendulum motion. The connecting rod can be firmly mounted on the piston 4 if the seal 101 compensates for the tipping of the piston 4 in the housing 100 caused by the interaction of the connecting rod 7a with the eccentric plate 7b. Otherwise the connecting rod can also be moveably mounted on the piston, whereby in that case the seal 101 then advantageously guarantees secure guiding of the piston 4 in the housing 100.

According to the invention, the movement means 7 in the embodiment shown in FIG. 1 is disposed in a second compression space 5 that is also formed by the housing 100 and closed off by the piston 4. In other words, the movement means 4, in this case the piston, separates the housing 100 of the compressor according to the invention into a first compression chamber and a second compression chamber, whereby the compression means 4 acts upon the gas volume of both compression chambers when it is moved by the movement means 7.

With reference to the second compression space 5 a gas passage opening 6 is provided according to the invention from which a second gas, that may also be air, is able to flow out of the second compression space 5 through the gas passage opening 6 when the piston 4 reduces the size of the second compression space and to flow into the second compression space 5 when the piston 4 enlarges the second compression space. Pressure variations are superimposed upon the gas volume located in the second compression space 5 and on a gas volume optionally connected to the second compression space 5, which will be explained in greater detail below, when the piston 4 moves backwards and forwards according to the double arrows in FIG. 1.

According to the invention, the compressor shown in FIG. 1 is used on the one hand to generate a pressure medium flow to generate an aerosol and, on the other hand, to provide pressure variations in a gas volume that can be superimposed upon a main aerosol flow that is generated by means of the continuous pressure medium flow.

In order to connect an inhalation therapy device appropriately, the gas outlet means 3 advantageously has a connecting sleeve 3a so that it is, for example, possible to connect a hose line to a nebulizing nozzle in an inhalation therapy device. A connecting sleeve 6a for a hose line is, moreover, advantageously provided at the gas passage opening 6 of the second compression chamber 5 with which the pressure variations are applied to the inhalation therapy device in order to be superimposed there upon the aerosol flow.

By integrating the movement means according to the invention into the one compression chamber, the second compression chamber 5 in FIG. 1, a compact compressor is realized that provides the two pressure medium sources required in one constructional unit. A single electromotor (not shown) is needed to drive the two compressor means, use advantageously being made of the ability of the electromotor to drive the piston 4 of the compressor according to the invention with a frequency through which pressure variations are generated in every therapeutically desired frequency range. At the same time an adequate pressure medium flow is generated by means of the first compression space and of the gas inlet and gas outlet means 2 and 3 respectively.

It is possible by means of a suitable choice of the materials of the connecting rod 7a and the eccentric plate 7b to achieve operation with little friction and thus little loss without the presence in the compression space of contaminating abraded material or lubricants taken up by the movement means according to the invention. This is necessary since the pressure variations produced in the compression space are superimposed upon an aerosol flow that is conveyed to a patient for therapeutic purposes. For this reason contamination must always be prevented. Various plastics are suitable materials for the connecting rod. Zinc is a suitable material for the eccentric plate.

Figure 2:
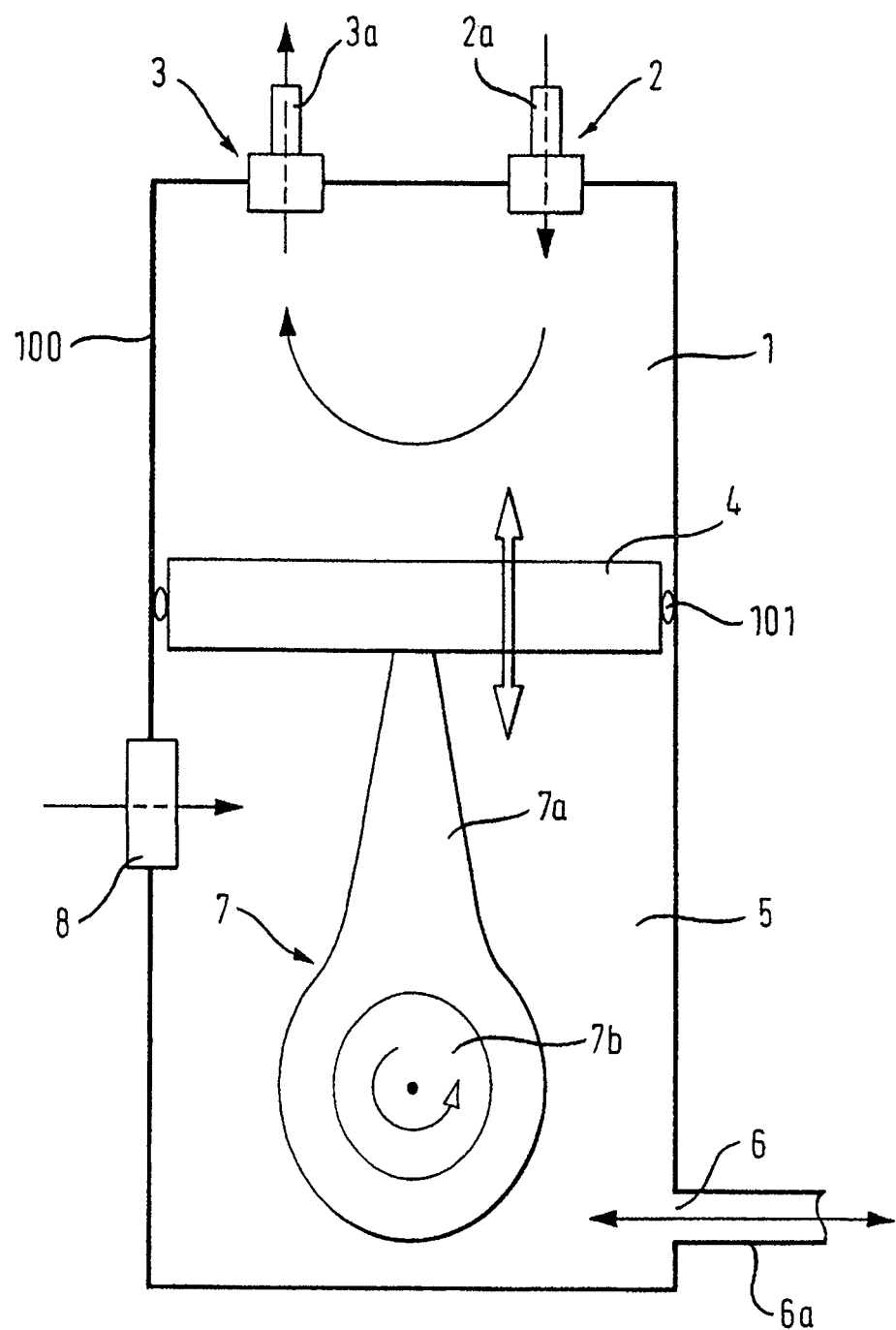

FIG. 2 shows another embodiment of a compressor for inhalation therapy devices according to the invention that substantially corresponds to the first embodiment and reference is therefore made to the above description of the first embodiment. FIG. 2 therefore also uses the same reference numerals. As distinct from the first embodiment, the second embodiment provides a gas inlet means 8 that permits the controlled penetration of the second gas, for example, ambient air, into the second compression chamber 5 when discharges or losses occur in the gas volume provided with pressure variations. The control of the entry of the second gas through the gas inlet means 8 occurs for example by means of an upstream inlet valve that will be described below. If there are intended discharges of gas or gas losses in the second embodiment in respect of the gas volume subjected to pressure variations, the upstream location of the inlet valve ensures, from a preset pressure onwards, that the second gas, for example ambient air, is able to flow on into the second compression chamber 5 and compensate for the discharge or loss.

Figure 3:
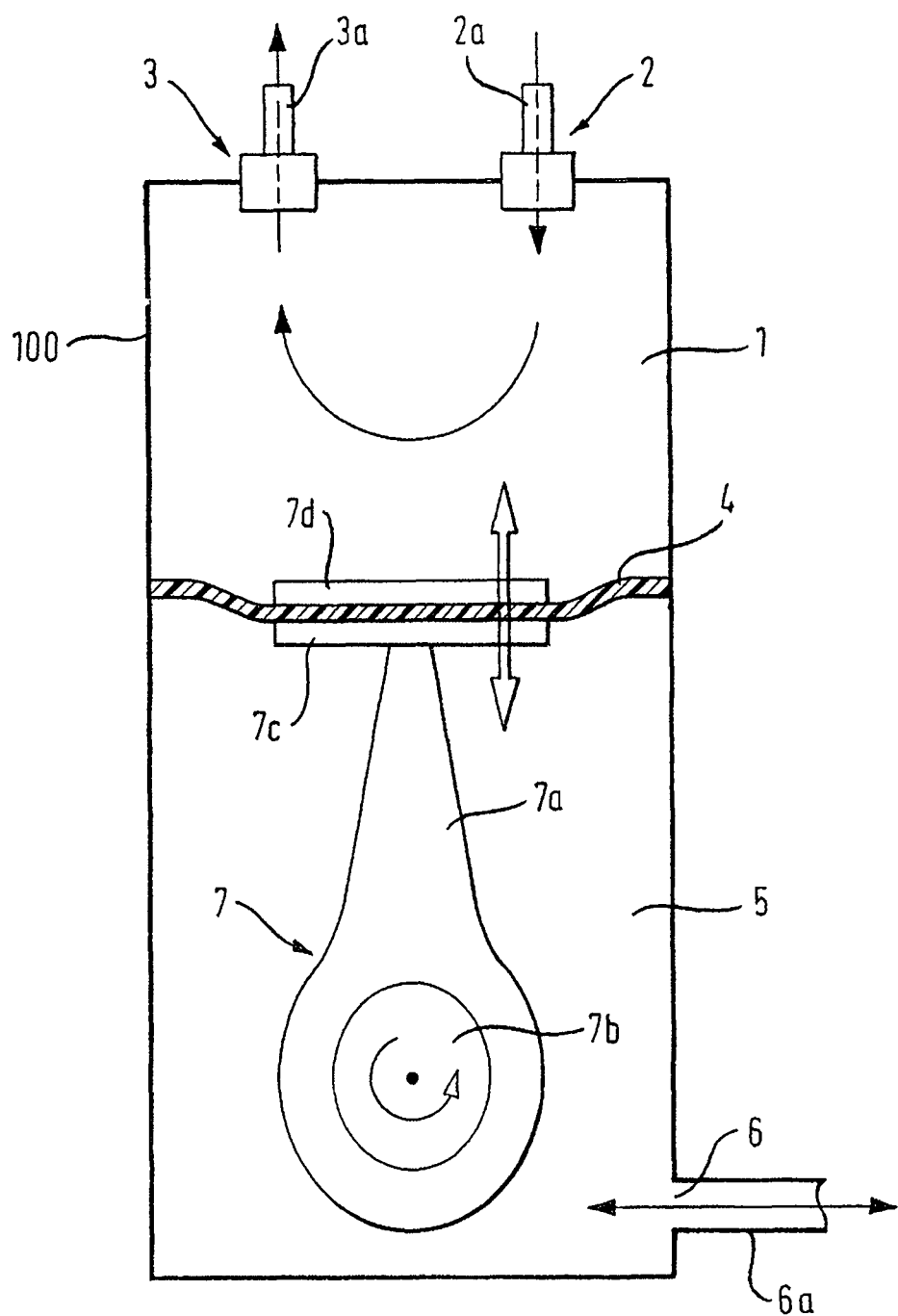

FIG. 3 shows a third embodiment of a compressor according to the invention that substantially corresponds to the structure of the first embodiment, and reference is therefore made to the above description relating to FIG. 1. FIG. 3 also uses the same reference numerals. As distinct from the first embodiment, the compressor according to the third embodiment is provided with a diaphragm as compression means 4 that is mounted on the housing and that divides the housing 100 into the first and second compression space 1 and 5 respectively. The diaphragm is lodged between two plates 7c and 7d that can be considered part of the movement means 7. When the two plates 7c and 7d are moved backwards and forwards by the connecting rod 7a according to the double arrows in FIG. 3, the diaphragm is also displaced out of its rest position, resulting in the compression and expansion movements in respect of the first compression chamber 1 and the second compression chamber 5 respectively. Otherwise the mode of action of the third embodiment corresponds entirely to the first embodiment and reference is therefore once again made in respect of the mode of action to the descriptions in connection with the first embodiment.

It is moreover evident that also the gas inlet means 8, which was described in connection with the second embodiment, can be provided in the case of a compressor according to the third embodiment.

Figure 4:
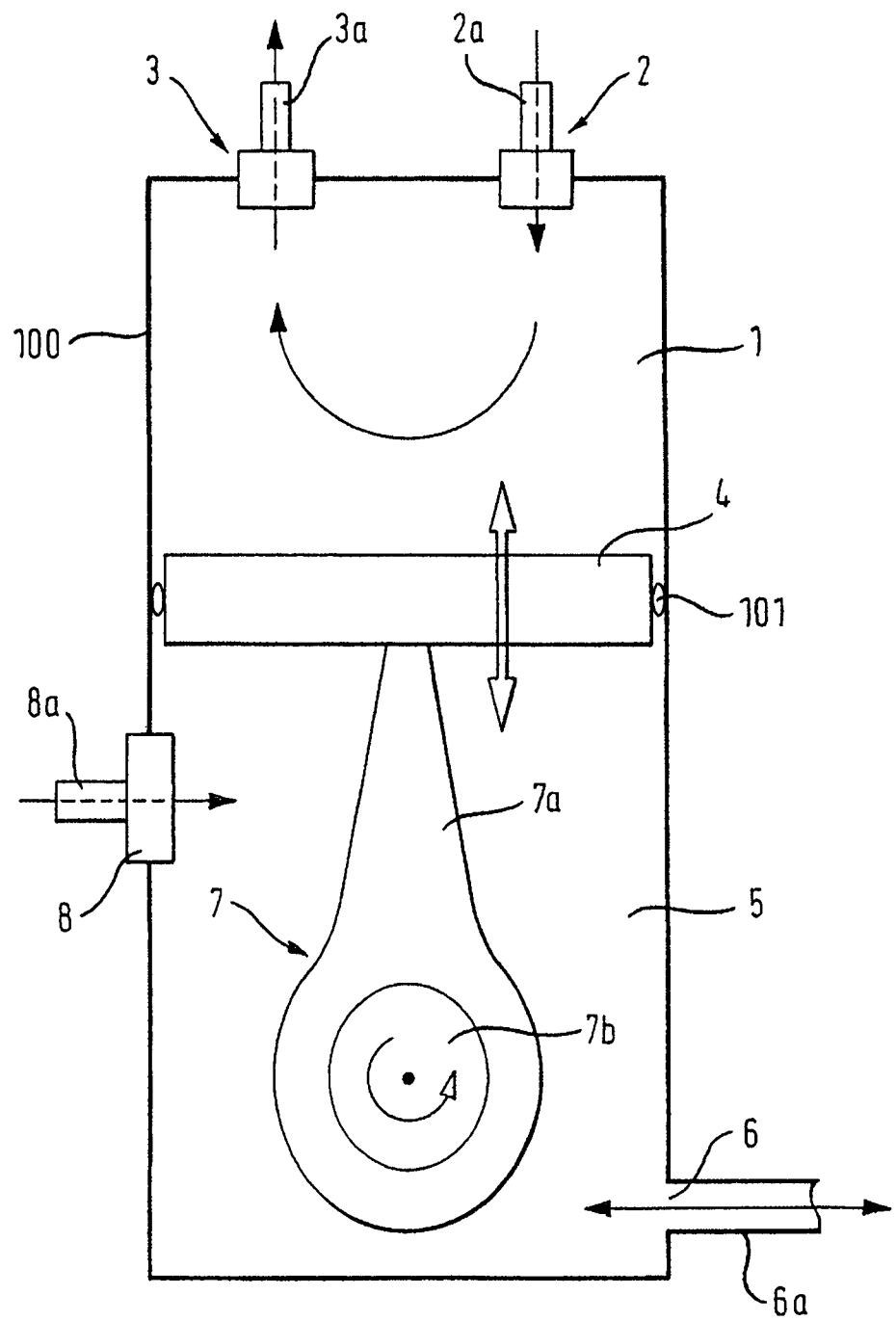

FIG. 4 shows a fourth embodiment of a compressor according to the invention that substantially corresponds to the structure of the second embodiment and reference is therefore made to the above description relating to FIG. 2. FIG. 4 also uses the same reference numerals. As distinct from the second embodiment, the gas inlet means 8 comprises a connection 8a for a hose line, so that a therapeutically or diagnostically active gas can be supplied as second gas to the second compression chamber 5. Also in this case the therapeutically or diagnostically active gas enters through the gas inlet means 8 in controlled form, for example only as from a specific pressure, it being possible to achieve this by means of an already mentioned, upstream gas inlet valve.

It should be noted here that it is also possible in all embodiments to connect a hose line to the gas inlet means 2 to supply a therapeutically or diagnostically active gas or gas/air mixture that is provided by means of the compressor according to the invention as a continuous pressure medium flow to the connecting sleeve of the gas outlet means 3. For this purpose the gas inlet means 2 comprises for example a connecting sleeve 2a.

Figure 5:
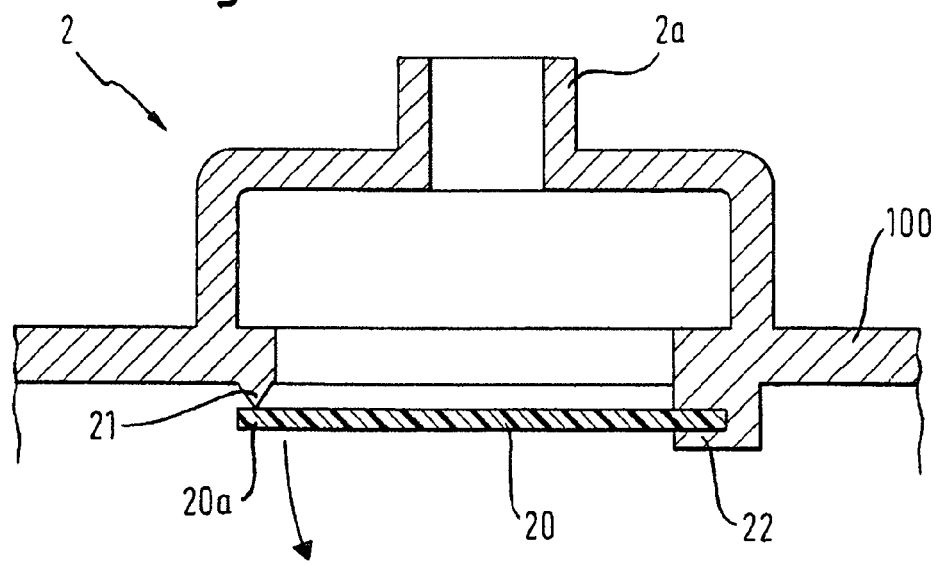

FIG. 5 shows by way of example an inlet valve that is suitable for disposal in the gas inlet means 2 of an inhalation therapy device compressor according to the invention. The inlet valve shown by way of example in FIG. 5 comprises a valve element 20 that is secured in relation to a valve seat 21 with a securing means 22 in such a way that it can only at its free end 20a become detached from the valve seat 21 when the first gas, for example ambient air, or the gas/air mixture referred to above, flows to the gas inlet means. This occurs when the compression means 4 of the compressor according to the invention generates a negative pressure in the first compression chamber 1.

Figure 6:
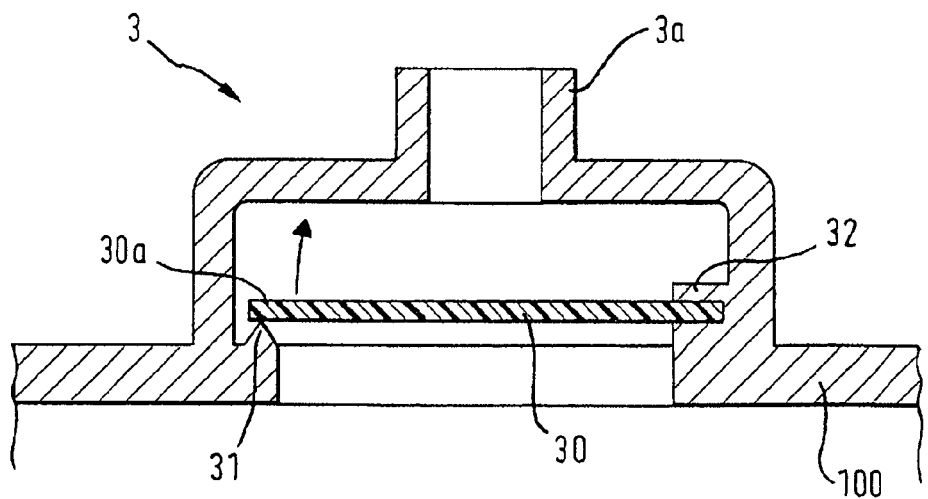

As a counterpart to the inlet valve shown in FIG. 5, FIG. 6 shows an outlet valve that is provided in the gas outlet means 3 of the compressor according to the invention and that comprises a valve element 30 that lies against a valve seat 31 and is retained by an anchorage 32. When the compression means 4 generates an overpressure in the compression chamber 1, the free end 30a of the valve element 30 of the outlet valve is lifted off the valve seat 31 so that the compressed gas or gas/air mixture can escape through the gas outlet means 3.

Figure 7:
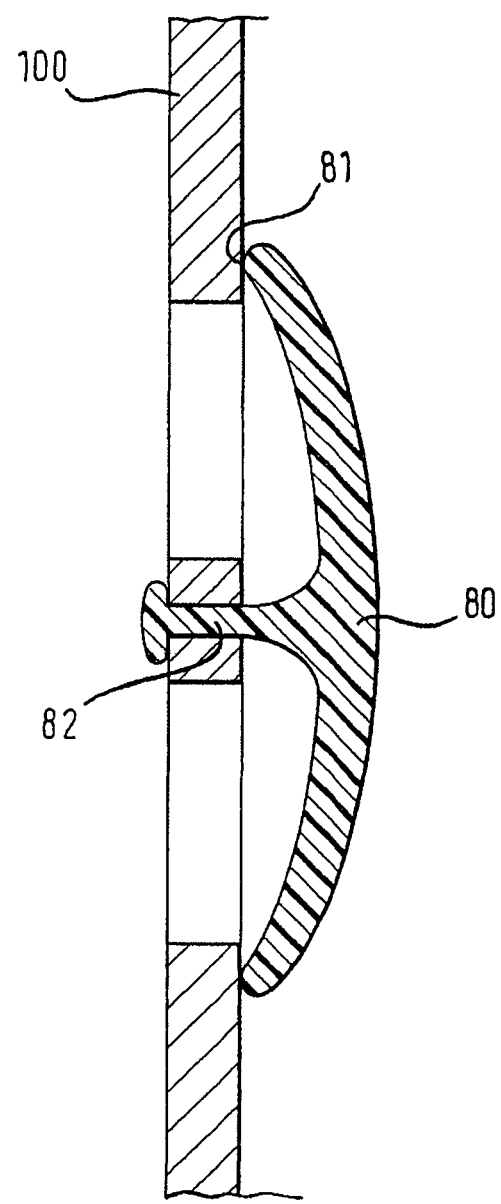

FIG. 7 shows by way of example an upstream inlet valve that is provided in the gas inlet means 8 that can be provided with reference to the second compression chamber 5 in a compressor according to the invention. The valve element 80 has a domed circular basic shape and is fixed by means of a securing stud 82 relative to a valve seat 81. When the negative pressure in the second compression chamber 5 falls below a value that corresponds to the initial load as a result of the movement of the compression means 4 and as a result of discharges or losses in gas volume, the second gas, for example air or the above-mentioned gas/air mixture flows on into the second compression chamber 5.

As already mentioned at the outset, the movement means 7, which in the four embodiments described is disposed in the second compression space 5, can be disposed in the first compression space 1, provided the first compression space is designed to be sufficiently tight. It should be noted in this connection that the pressures and flow volumes achieved are very much higher in comparison with the second compression space, with the result that different, higher demands are made of the tightness of the first compression space than of the tightness of the second compression space. However, provided the tightness is guaranteed by technical measures known to the person skilled in the art, there is nothing against disposing the movement means in the first compression space.

The compressor according to the invention can not only be used in association with inhalation therapy devices that comprise a nebulizing nozzle, but also with other nebulizers, for example diaphragm nebulizers such as described for example in EP 1 304 130 A. In this case the continuous pressure medium flow is not used to generate the aerosol, but to generate a basic aerosol flow by mixing the aerosol generated by the diaphragm nebulizer or ultrasound nebulizer in the pressure medium flow. The pressure variations generated by means of the compressor according to the invention are then superimposed upon the basic aerosol flow generated thereby.

The invention claimed is:

1. Inhalation therapy device compressor for an inhalation therapy device having
    a housing with a first compression space and a second compression space;
    a gas inlet means for the inflow of a first gas into the first compression space;
    a gas outlet means for the outflow of the first gas from the first compression space, and connected to the inhalation therapy device to generate a pressure medium flow;
    the second compression space being isolated from gas communication with the first compression space by a compression means, that closes off the first compression space in such a manner that, on moving the compression means, the first gas is conveyed into the first compression space via the gas inlet means and out of the first compression space via the gas outlet means;
    a movement means integrally disposed in the second compression space, comprising an eccentric plate driven by an electromotor and a connecting rod connected between the eccentric plate and the compression means, for moving the compression means backwards and forwards;
    a single gas passage opening, in gas communication with the second compression space, through which a second gas flows out from the second compression space when the compression means reduces the second compression space and through which the second gas flows into the second compression space when the compression means enlarges the second compression space, so that bi-directional pressure variations, resulting from the movement of the compression means in the second compression space, are applied to the second gas and pass through the gas passage opening; and
    a hose line, provided at the gas passage opening, with which the pressure variations from the movement of the compression means are applied to the inhalation therapy device and are superimposed upon the pressure medium flow.

2. Inhalation therapy device compressor according to claim 1, wherein the gas inlet means comprises an inlet valve.

3. Inhalation therapy device compressor according to claim 2, wherein a connection is provided at the gas inlet means to supply the first gas to the compressor.

4. Inhalation therapy device compressor according to claim 3, wherein the connection is a connecting sleeve for a hose line.

5. Inhalation therapy device compressor according to claim 1, wherein the gas outlet means comprises an outlet valve.

6. Inhalation therapy device compressor according to claim 5, wherein a connection is provided at the gas outlet means to remove the first gas from the compressor.

7. Inhalation therapy device compressor according to claim 6, wherein the connection is a connecting sleeve for a hose line.

8. Inhalation therapy device compressor according to claim 1, wherein a gas inlet means is provided that permits the controlled entry of the second gas into the second compression space.

9. Inhalation therapy device compressor according to claim 8, wherein the gas inlet means comprises an inlet valve.

10. Inhalation therapy device compressor according to claim 8, wherein a connection is provided at the gas inlet means to supply the second gas to the compressor.

11. Inhalation therapy device compressor according to claim 10, wherein the connection is a connecting sleeve for a hose line.

12. Inhalation therapy device compressor according to claim 1, wherein the compression means is a piston.

13. Inhalation therapy device compressor according to claim 1, wherein the compression means is a diaphragm.

14. Inhalation therapy device compressor according to claim 1, wherein the first gas and/or the second gas is air or a therapeutically active gas or a gas/air mixture.

15. Inhalation therapy device compressor for an inhalation therapy device comprising:
 a housing with a first compression space and a second compression space;
 the second compression space being isolated from gas communication with the first compression space;
 a gas inlet for the inflow of a first gas into the first compression space;
 a gas outlet for the outflow of the first gas from the first compression space, and connected to the inhalation therapy device to generate a pressure medium flow;
 a piston, that closes off the first compression space in such a manner that, on moving the piston, the first gas is conveyed into the first compression space via the gas inlet and out of the first compression space via the gas outlet;
 a single gas passage opening, in gas communication with the second compression space, through which a second gas flows out from the second compression space when the piston reduces the second compression space and through which the second gas flows into the second compression space when the piston enlarges the second compression space, so that bi-directional pressure variations, resulting from the movement of the piston in the second compression space, are applied to the second gas and pass through the gas passage opening;
 a hose line, provided at the gas passage opening, with which the pressure variations from the movement of the piston are applied to the inhalation therapy device and are superimposed upon the pressure medium flow; and
 a movement mechanism that is disposed outside the first compression space and inside the second compression space and that is associated with the piston in such a way that the piston is movable by the movement mechanism.

* * * * *